United States Patent
Koch (10) Patent No.: US 12,357,524 B2
(45) Date of Patent: Jul. 15, 2025

(54) QUICKLY ADJUSTABLE COMPACT SPINDLE TRACTION MECHANISM WITH SELF-LOCKING FOR USE IN SURGICAL INTERVENTIONS

(71) Applicant: MAQUET GMBH, Rastatt (DE)

(72) Inventor: Guido Koch, Karlsruhe (DE)

(73) Assignee: MAQUET GMBH (DE)

( * ) Notice: Subject to any disclaimer, the term of this patent is extended or adjusted under 35 U.S.C. 154(b) by 1186 days.

(21) Appl. No.: 16/634,747

(22) PCT Filed: Aug. 2, 2018

(86) PCT No.: PCT/EP2018/071067
§ 371 (c)(1),
(2) Date: Jan. 28, 2020

(87) PCT Pub. No.: WO2019/025570
PCT Pub. Date: Feb. 7, 2019

(65) Prior Publication Data
US 2020/0206056 A1    Jul. 2, 2020

(30) Foreign Application Priority Data
Aug. 4, 2017    (DE) .................... 10 2017 117 767.1

(51) Int. Cl.
*A61G 13/12*    (2006.01)
*A61B 17/64*    (2006.01)
(Continued)

(52) U.S. Cl.
CPC ........ *A61G 13/129* (2013.01); *A61B 17/8869* (2013.01); *A61G 13/125* (2013.01);
(Continued)

(58) Field of Classification Search
CPC .............. A61G 13/129; A61G 13/0036; A61G 13/0063; A61G 13/0081; A61G 13/123;
(Continued)

(56) References Cited

U.S. PATENT DOCUMENTS 4,342,309 A * 8/1982 Eftekhar ............ A61B 17/1697
606/104
4,747,319 A * 5/1988 Sakuta .................... F16H 25/20
74/89.41
(Continued)

FOREIGN PATENT DOCUMENTS

CN        2647507 Y      10/2004
CN     103307239 A       9/2013
(Continued)

OTHER PUBLICATIONS

CN Office Action for Application No. 201880048723.5.
(Continued)

*Primary Examiner* — Rachael E Bredefeld
*Assistant Examiner* — Seth R. Brown
(74) *Attorney, Agent, or Firm* — Frost Brown Todd LLP (57) ABSTRACT

A self-locking spindle traction mechanism for use in surgical procedures has a longitudinal axis (L). The mechanism may include an operating end, a connecting end for connecting a surgical accessory, and a threaded spindle drive. The spindle drive may include a spindle having an external thread, and a spindle nut that is seated on the spindle and has an internal thread. The mechanism may include a slide that is movable along the longitudinal axis by a relative rotation between the spindle and the spindle nut, a drive device that is situated on the operating end for rotationally driving the threaded spindle drive, and a gear. The gear may be connected between the drive device and the threaded spindle drive, so that the gear is configured for stepping up the speed of a (Continued)

rotational movement of the drive device and delivering it to the threaded spindle drive.

20 Claims, 4 Drawing Sheets (51) Int. Cl.
*A61B 17/88* (2006.01)
*A61F 5/042* (2006.01)
*A61F 5/37* (2006.01)
*F16H 25/20* (2006.01)
*F16H 25/24* (2006.01)
*F16M 13/02* (2006.01)

(52) U.S. Cl.
CPC ..... *A61G 13/1285* (2013.01); *A61G 13/1295* (2013.01); *F16H 25/2454* (2013.01); *F16M 13/022* (2013.01); *A61B 17/6408* (2013.01); *A61F 5/042* (2013.01); *A61F 5/3761* (2013.01); *F16H 2025/2031* (2013.01); *F16H 2025/204* (2013.01); *F16H 2025/2062* (2013.01); *F16H 2025/2087* (2013.01)

(58) Field of Classification Search
CPC .............. A61G 13/1245; A61G 13/125; A61G 13/1285; A61G 13/1295; A61G 2210/10; A61G 13/0045; A61G 13/0072; A61G 13/009; A61G 13/02; F16H 25/2454; F16H 2025/2031; F16H 2025/204; F16H 2025/2062; F16H 25/2006; F16M 13/022; A61B 17/6408; A61B 17/66; A61F 5/3761; A61F 5/042; A61F 5/04; A61H 1/0218; A61H 1/0222; A61H 1/0237; A61H 1/0244; A61H 1/0274; A61H 1/0281

USPC .................................... 475/257, 900
See application file for complete search history.

(56) References Cited

U.S. PATENT DOCUMENTS

| | | | | |
|---|---|---|---|---|
| 4,802,464 | A * | 2/1989 | Deprez | A61F 5/04 5/613 |
| 2007/0251011 | A1* | 11/2007 | Matta | A61G 13/1205 5/624 |
| 2008/0020893 | A1* | 1/2008 | Frieb-Preis | F16H 25/20 476/64 |
| 2010/0282008 | A1* | 11/2010 | Knudsen | G01D 5/04 74/89.23 |
| 2010/0282009 | A1 | 11/2010 | Knudsen et al. | |
| 2015/0366622 | A1* | 12/2015 | Wyslucha | F16D 41/105 5/648 |
| 2016/0346147 | A1* | 12/2016 | Brown | A61F 5/3769 |

FOREIGN PATENT DOCUMENTS

| | | |
|---|---|---|
| CN | 105193576 A | 12/2015 |
| DE | 202009003314 U1 | 5/2009 |
| DE | 202011106149 U1 | 2/2013 |
| DE | 102013202700 A1 | 9/2013 |
| EP | 2982880 A2 | 2/2016 |

OTHER PUBLICATIONS

International Search Report issued on Nov. 15, 2018 during the prosecution of corresponding PCT application No. PCT/EP2018/071067, 2 pages.

Office Action mailed Oct. 5, 2022 in EP Application No. 18762228.7, 6 pages.

* cited by examiner

QUICKLY ADJUSTABLE COMPACT SPINDLE TRACTION MECHANISM WITH SELF-LOCKING FOR USE IN SURGICAL INTERVENTIONS

BACKGROUND OF THE DISCLOSURE

The present disclosure relates to a spindle traction mechanism that may be used, for example, with an extension beam on an operating table.

These types of extension beams usually include a bar on which a holder for a patient's foot is movably mounted by means of a displaceable strut or the like, with a spindle traction mechanism situated in between. After the strut is fixed, for some surgical applications it may be desirable to move the holder and the patient's foot further in the direction of a longitudinal axis of the patient's leg by means of the spindle traction mechanism, for example in order to extend a hip joint of the patient. This linear adjustment movement is generally achieved via a threaded spindle drive of the spindle traction mechanism which is operable by the user via a hand crank. In the process, relatively high axial forces act on the spindle traction mechanism; once the axial position of the patient's foot is set, it is important for it to be maintained, i.e., for the spindle traction mechanism to be self-locking. The self-locking may be achieved by using a spindle, having a relatively low pitch, in the spindle traction mechanism. Self-locking is always present when the friction force is a function of the applied axial force, and the associated friction torque is always greater than the torque generated by the axial force.

However, the low pitch means a large number of spindle revolutions in order to travel the necessary distance. This is very laborious for the user. However, when, for the same spindle diameter, a spindle with higher pitch is used for which fewer spindle revolutions are required for a given displacement travel, the traction spindle is no longer self-locking, since due to the larger pitch angle, the friction forces between the spindle and the spindle nut are no longer sufficient to prevent the traction spindle from automatically rotating under axially acting forces. Despite the higher pitch, the self-locking could be achieved by increasing the diameter of the spindle. However, this would make the spindle traction mechanism undesirably heavy and bulky.

The user perceives a comfortable feeling when a 10-15 mm lift is carried out per crank revolution. However, a threaded spindle with this pitch of 10-15 mm would have to have a diameter greater than 40 mm in order to be self-locking. The spindle traction mechanism would thus have an unacceptably high weight and large size. This would also be overdimensioned for the loads that occur.

OVERVIEW OF THE DISCLOSURE

The object of the present disclosure, therefore, is to provide a spindle traction mechanism that may be quickly moved, but which is self-locking and compact.

The above object is achieved by a self-locking spindle traction mechanism for use in surgical procedures, having an elongated extension that defines a longitudinal axis, the spindle traction mechanism comprising:
  an operating end for operating the spindle traction mechanism;
  a connecting end for connecting a surgical accessory, for example a patient foot holder, to the spindle traction mechanism;
  a threaded spindle drive with
    a) a spindle having an external thread that extends along the longitudinal axis; and
    b) a spindle nut that is seated on the spindle and that has an internal thread that engages with the external thread;
  a slide that is movable along the longitudinal axis by a relative rotation between the spindle and the spindle nut;
  a drive device that is situated on the operating end for rotationally driving the threaded spindle drive; and
  a gear that is connected between the drive device and the threaded spindle drive, wherein the gear is configured for stepping up the speed of a rotational movement of the drive device and delivering it to the threaded spindle drive.

The spindle traction mechanism may be moved quickly due to the gear that steps up the speed. The patient's foot may thus be positioned at a desired location quickly and efficiently with relatively few revolutions of the drive device.

The spindle traction mechanism according to the disclosure preferably has one, multiple, or all of the following features, provided that this is technically feasible:
  a restraining device for inhibiting the relative rotation between the spindle and the spindle nut when a tensile force is applied to the connecting end along the longitudinal axis;
  a housing that accommodates the threaded spindle drive, wherein the restraining device has a friction pair, wherein the friction pair is made up of a first contact surface situated on the housing, and a second contact surface situated on the threaded spindle drive, opposite from the first contact surface, wherein when a tensile force is exerted on the connecting end along the longitudinal axis, the second contact surface is supported on the first contact surface in such a way that frictional resistance is present that prevents an automatic relative rotation between the spindle and the spindle nut due to the tensile force;
  the first and the second contact surfaces extend essentially perpendicularly with respect to the longitudinal axis;
  the spindle is stationarily and rotatably situated in the housing, and the spindle nut is rotatably fixedly connected to the slide, the second contact surface being situated on the spindle;
  the housing includes a spindle bearing sleeve on which the first contact surface is formed, and wherein the spindle has a contact disk, rotatably fixedly connected thereto, on which the second contact surface is formed;
  the gear includes a planetary gear;
  the gear is stepped up in such a way that one revolution of the drive device corresponds to at least two revolutions of the threaded spindle drive, preferably in such a way that one revolution of the drive device corresponds to 3.5 revolutions of the threaded spindle drive;
  a diameter of the spindle (32) is less than 20 mm, in particular less than 15 mm;
  a diameter of the spindle (32) is 12 mm and a pitch of the spindle is 3 mm.

The spindle traction mechanism may preferably have an additional restraining device. Such an additional restraining device guarantees self-locking of the spindle traction mechanism. As a result, the self-locking no longer has to be ensured solely by precisely selecting the dimensioning of the external thread of the spindle. Accordingly, the spindle traction mechanism may be provided with a standard commercially available spindle that does not have to be 100% self-locking under all conceivable operating conditions. The precisely dimensioned restraining device takes over the reliable self-locking.

The restraining device may generate a friction force that is proportional to the load that is applied to the spindle traction mechanism. Thus, with an increased tensile force on the slide, an increased friction force is achieved by the restraining device so that self-locking is provided, even under high load. The inhibiting effect of the restraining device is added to the inhibiting effect of the external thread of the spindle.

According to some embodiments, the housing may include a spindle bearing sleeve, wherein a contact disk that is rotatably fixedly connected to the spindle rests against the spindle bearing sleeve, so that the contact disk together with a contact surface of the spindle bearing sleeve forms the restraining device. The housing may thus have a compact design. The inhibiting effect that is produced may be influenced by changing the surface area of the friction surfaces between the contact disk and the contact surface.

According to some embodiments, the gear may include a planetary gear. A compact design of a gear unit may thus be achieved, and it may be ensured that the rotational axis of the drive device coincides with the rotational axis of the threaded spindle drive.

The gear may be stepped up in such a way that one revolution of the drive device corresponds at least to two revolutions of the threaded spindle drive. The gear is preferably stepped up in such a way that one revolution of the drive device corresponds to 3.5 revolutions of the threaded spindle drive.

According to some embodiments, the threaded spindle drive may have a trapezoidal spindle. A diameter of the spindle may be less than 20 mm, for example, in particular less than 15 mm. The spindle traction mechanism may thus have a compact design, and it is not necessary, for example, to provide a stator tube having a large inner diameter in which the spindle is rotatably accommodated.

In one exemplary embodiment, the diameter of the spindle may be 12 mm, and the pitch of the spindle may be 3 mm. Such a spindle is essentially self-locking. In combination with a gear having a gear ratio of 3.5 revolutions of the threaded spindle drive per revolution of the drive device, a displacement travel of the drive device of 10.5 mm per revolution may then be achieved.

The present disclosure likewise relates to an extension beam for an operating table, comprising:
 a bar that is mountable on the operating table;
 a displaceable strut that is displaceable along a longitudinal axis of the bar, and that bears a holder for a foot of a patient; and
 a spindle traction mechanism as defined above for adjusting the holder for the foot of the patient relative to a position of the strut in a direction essentially parallel to a longitudinal axis of the spindle traction mechanism.

According to a further aspect, an extension beam for an operating table is provided which includes a bar that is mountable on the operating table, and a displaceable strut that is displaceable along a longitudinal axis of the bar and that bears a holder for a foot of a patient. Furthermore, the extension beam includes a spindle traction mechanism as described above for adjusting the holder for the foot of the patient relative to a position of the strut in a direction essentially parallel to a longitudinal axis of the spindle traction mechanism.

BRIEF DESCRIPTION OF THE DRAWINGS

Exemplary embodiments of the present disclosure are described below with reference to the appended drawings, in which identical or corresponding elements are denoted in each case by the same reference numerals.

DETAILED DESCRIPTION

Exemplary embodiments of the present disclosure are described in the following description, with reference to the drawings. The drawings are not necessarily true to scale, and are intended to merely schematically illustrate the particular features.

It is noted that the features and components described below may be combined with one another in each case, regardless of whether they have been described in conjunction with an individual embodiment. The combination of features in the particular embodiments is used solely to illustrate the basic design and the operating principle of the claimed device.

Figure 1:
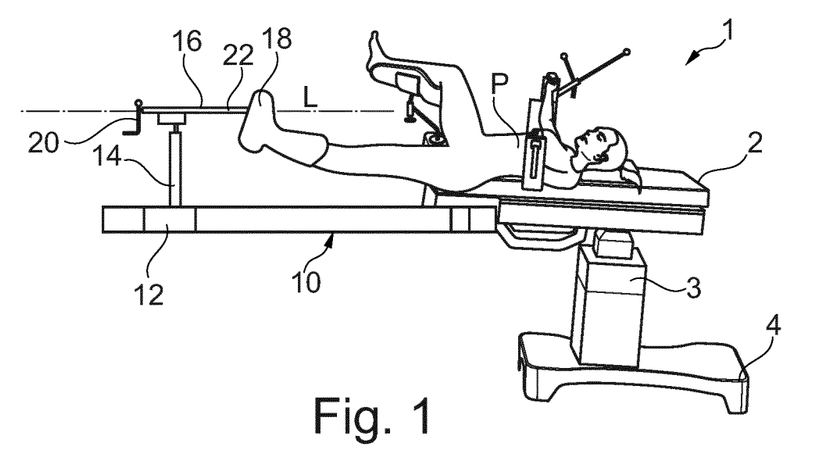
FIG. 1 shows an illustration of an operating table having an extension beam in which a spindle traction mechanism according to one embodiment of the present disclosure is used.

As illustrated in FIG. 1, an operating table 1 includes a patient support surface 2, a column 3, and a base 4. For carrying out orthopedic surgical procedures, an extension beam 10 may be used, by means of which the leg of a patient P may be fixed in a desired position. For this purpose, a displaceable strut 14 may be mounted on a bar 12 of the extension beam 10, the strut bearing a spindle traction mechanism 16 that is connected to a holder 18 for a patient's foot.

When the displaceable strut 14 is fixed in a suitable position on the bar 12, traction may thus be exerted on the patient's foot via the spindle traction mechanism 16 in a direction along the longitudinal axis L of the spindle traction mechanism 16, for example to extend a hip joint of the patient P. The displacement path of the spindle traction mechanism 16 may be up to 20 cm in order to exert traction on the clamped extremity.

For this purpose, a slide 22 of the spindle traction mechanism 16 is generally translationally moved. The slide 22 must remain under tensile load at the set position; i.e., the spindle traction mechanism must have a self-locking design.

Figure 2:
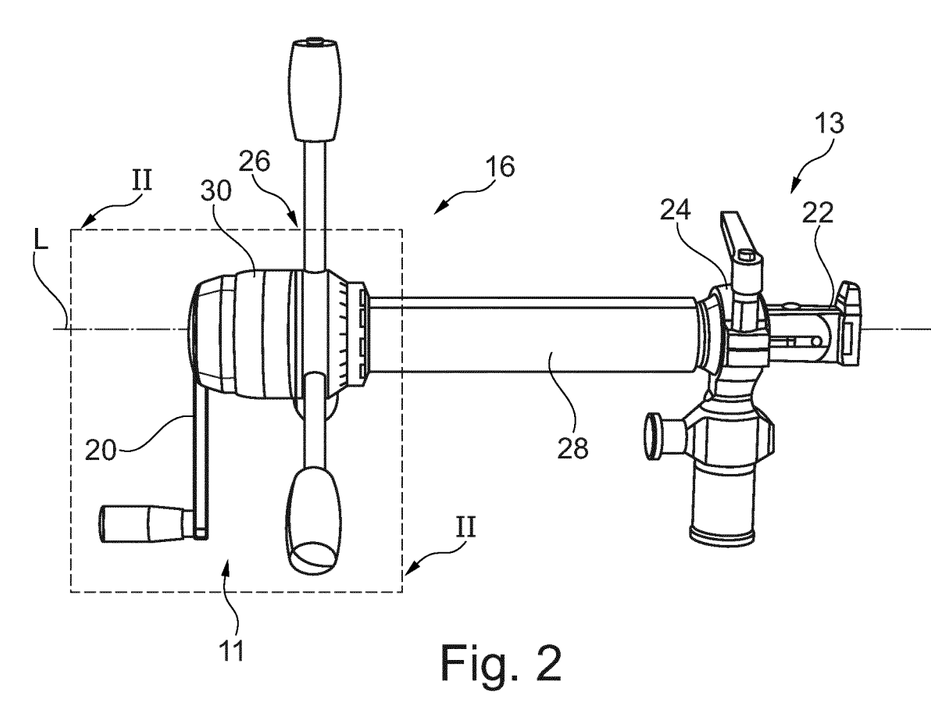
FIG. 2 shows a spindle traction mechanism according to one embodiment of the present disclosure.

FIG. 2 shows an illustration of the spindle traction mechanism 16 from FIG. 1 according to one embodiment of the present disclosure.

The spindle traction mechanism 16 has an operating end 11 at which the spindle traction mechanism may be operated by the user. The spindle traction mechanism likewise has a connecting end 13 for connecting a surgical accessory.

The spindle traction mechanism 16 is connectable to the displaceable strut 14 of the extension beam 10 (see FIG. 1) via a receiving sleeve 24. The holder 18 for a patient's foot may be fastened to the slide 22 of the spindle traction mechanism 16 at the connecting end 13 (see FIG. 1).

The spindle traction mechanism 16 also includes a drive device in the form of a hand crank 20, by means of which the slide 22 is movable in the direction of the longitudinal axis L of the spindle traction mechanism 16.

In addition to the adjustment in the longitudinal direction, a detent mechanism 26 may be provided on the spindle traction mechanism 16 which allows the slide 22 and the foot holder 18 fastened thereto to rotate about the longitudinal axis L. The detent mechanism 26 is not explained in greater detail in the present description, and is independent of the adjustment of the slide 22, described here, in the longitudinal direction.

The spindle traction mechanism 16 also includes a stator tube 28 which forms a portion of a housing of the spindle traction mechanism 16 and within which a threaded spindle drive is rotatably situated, as described in greater detail below. In addition, a gear 30 is situated between the hand crank 20 and the threaded spindle drive. A planetary gear is preferably used, so that the drive axis and the output axis of the gear 30 are both situated on the longitudinal axis L of the spindle traction mechanism.

Figure 3:
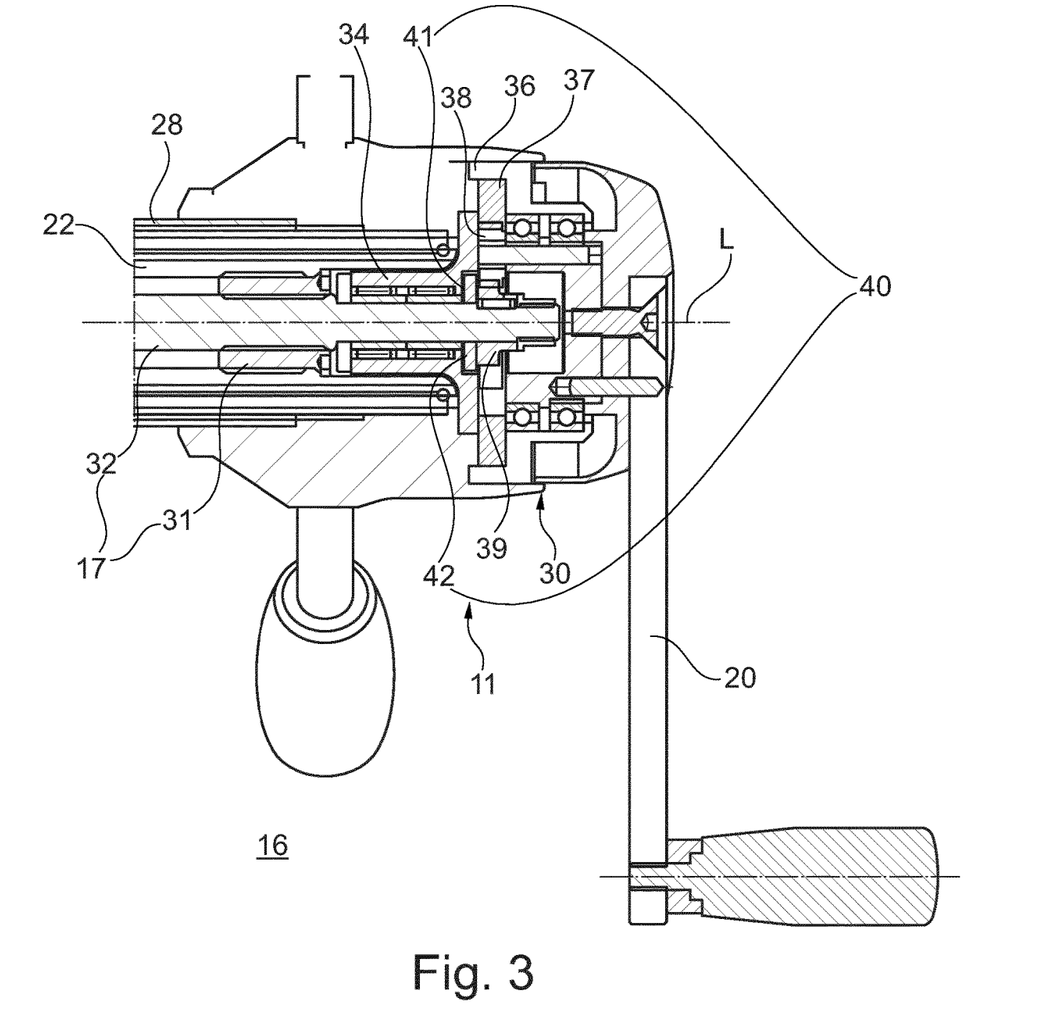
FIG. 3 shows a partial longitudinal section of the spindle traction mechanism from FIG. 2 according to the arrows II-II.
Figure 4:
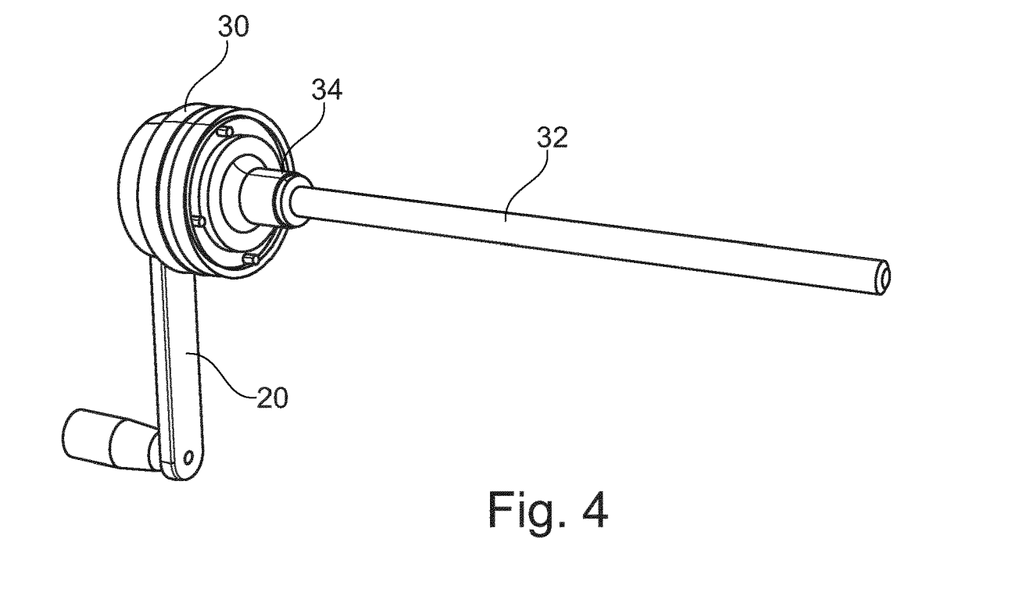
FIG. 4 shows several components of the spindle traction mechanism from FIG. 2.

FIGS. 3 and 4 show the internal design of the spindle traction mechanism 16 from FIG. 2. The threaded spindle drive 17 is apparent. The threaded spindle drive includes a spindle 32 that extends along the longitudinal axis L and is rotatably accommodated in the stator tube 28. The spindle 32 is supported in a spindle bearing sleeve 34. In the present embodiment, the spindle 32 is a trapezoidal spindle having a diameter of 12 mm and a pitch of 3 mm. The spindle 32 thus has an external thread that is self-locking under most operating conditions.

It is possible to use other types of threaded spindles, such as spindles having a V-thread or a buttress thread.

The threaded spindle drive 17 also has a spindle nut 31, seated on the spindle 32, having an internal thread that engages with the external thread of the spindle.

The slide 22 is movable along the longitudinal axis L via a relative rotation between the spindle 32 and the spindle nut 31.

In the present example, the spindle 32 is stationarily and rotatably situated in the stator tube 28, and the spindle nut 31 is rotatably fixedly and axially displaceably connected to the slide 22. In order to move the slide 22, the spindle 32 is rotated so that the spindle nut 31 moves linearly on the spindle 32.

However, it is also possible to design the threaded spindle drive in a kinematically reverse manner, so that the spindle nut is stationarily and rotatably situated, and the spindle is rotatably fixedly connected to the slide. In this case, the spindle together with the slide moves linearly relative to the spindle nut.

The spindle traction mechanism 16 preferably has an additional restraining device 40 for inhibiting the relative rotation between the spindle 32 and the spindle nut 31 when a tensile force is exerted on the connecting end 13 along the longitudinal axis L. This restraining device 40 has a friction pair 41, 42, the friction pair being made up of a first contact surface 41 situated on the housing, namely, on the spindle bearing sleeve 34, and a second contact surface 42, opposite from the first contact surface, situated on the threaded spindle drive 17. When a tensile force is then exerted on the connecting end 13 along the longitudinal axis L, the second contact surface 42 is supported on the first contact surface 41 in such a way that frictional resistance is present, which prevents automatic relative rotation between the spindle 32 and the spindle nut 31 due to the tensile force. This frictional resistance increases in proportion to the applied axial load. It is apparent from FIG. 3 that the first and the second contact surface 41, 42 extend essentially perpendicularly with respect to the longitudinal axis L. The surface areas of the contact surfaces are dimensioned in such a way that the self-locking is established with sufficient reliability.

In the present case, the second contact surface 42 is implemented in the form of a contact disk that is rotatably fixedly connected to the spindle 32.

In order to generate the required large displacement travel per crank revolution by use of the hand crank 20, in the embodiment shown a planetary gear 30 is situated between the hand crank and the spindle 32, and steps up the speed of the hand crank revolutions, so that the spindle 32 undergoes approximately 3.5 revolutions, for example, in one hand crank revolution, and the required displacement travel of the slide 22 per hand crank revolution is thus achieved.

Figure 5:
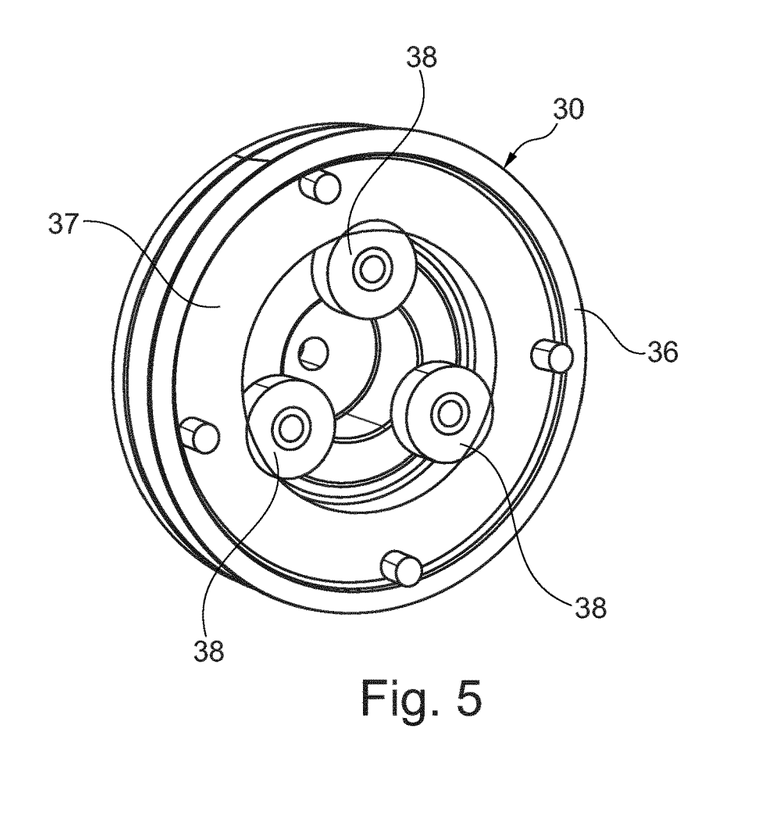
FIG. 5 shows a gear that may be used with the spindle traction mechanism from FIG. 2.

FIG. 5 shows one example of such a planetary gear 30. An annulus gear 36 is fixedly screwed into the stator tube 28, and a planet wheel carrier 37 is connected to the hand crank 20. In the example shown, the planet wheel carrier 37 drives three planet wheels 38, which in turn drive a sun wheel 39 (shown in FIG. 3) that is situated in the center and connected to the spindle 32. The rotational axis of the planet wheel carrier 37, and thus the rotational axis of the hand crank 20, coincides with the rotational axis of the sun wheel, and thus, with the rotational axis of the spindle 32.

Figure 6:
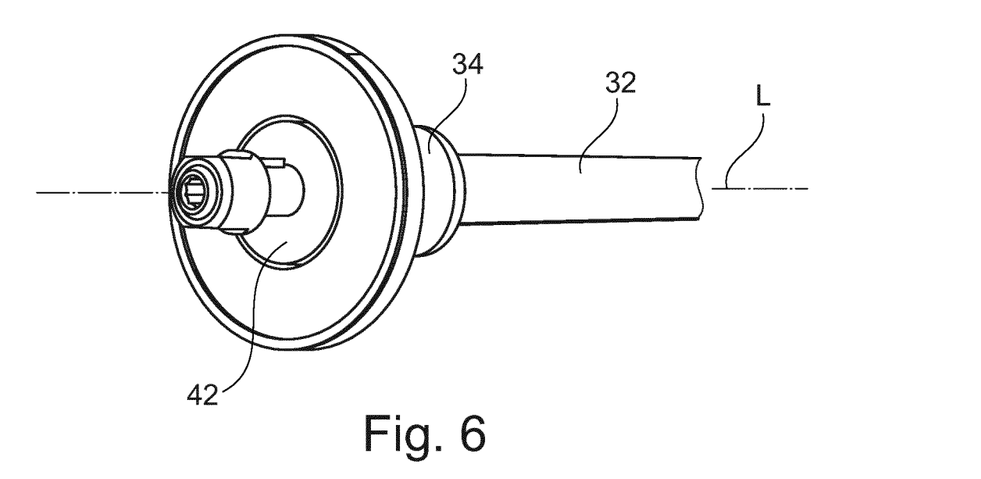
FIG. 6 shows several components for supporting the spindle for the spindle traction mechanism from FIG. 2.

FIG. 6 shows the mounting of the spindle 32 in the spindle bearing sleeve 34. The spindle bearing sleeve 34 is fixedly attached to the stator tube 28 or to some other part of the housing of the spindle traction mechanism 16.

The contact disk 42 is fastened to the spindle 32, and is thus rotatable relative to the spindle bearing sleeve 34. The spindle 32 is supported on the spindle bearing sleeve 34 on the contact surface 41 along the longitudinal axis L in the axial direction by means of the contact disk 42. The friction force between the contact disk 42 and the contact surface 41 of the spindle bearing sleeve 34 is proportional to the axial load applied to the spindle 32. The diameter of the contact disk 42 is selected to be large enough that the self-locking of the spindle traction mechanism 16 is achieved with the required reliability for all tensile forces that are to be expected during operation.

The present disclosure thus provides a spindle traction mechanism that is self-locking and that has a large displacement travel per crank revolution.

The above-described spindle traction mechanism allows good operator ergonomics, since on the one hand a user can achieve a relatively large displacement travel with relatively few revolutions of the hand crank, and on the other hand, self-locking of the traction spindle can be ensured, even under high tensile forces.

The large displacement travel per hand crank revolution which is appropriate for operation is achieved by use of the gear, which steps up the speed.

If the additional restraining device is also provided, when selecting the spindle of the threaded spindle drive it does not have to always be self-locking. It is thus possible to use spindles having a higher pitch. A higher spindle pitch has the advantage that the gear for stepping up to a higher speed may have a smaller gear ratio in order to achieve the appropriately large displacement travel. A compact gear having a simple design may thus be used.

In addition, the spindle traction mechanism of the present disclosure may also have the following features that allow self-locking of the spindle traction mechanism:
 a spindle 32 having a diameter of 25 mm or less, 20 mm or less, or 15 mm or less;
 the spindle has a thread pitch of 2 mm or greater, 2.5 mm or greater, or 3 mm or greater;

the dimensions, diameters, and thread pitches of the threaded spindle and the spindle nut are such that the spindle traction mechanism, not just due to its thread, is completely self-locking without the additional restraining device 40. For example, the spindle traction mechanism is not completely self-locking without the restraining device 40 if the threaded spindle 32 is exposed to axial forces that are to be expected during use;

the restraining device has a first surface 41 and a second surface 42 with different shapes and configurations;

the two surfaces 41 and 42 are positioned opposite one another in such a way that axial traction on the spindle 32 pushes the two surfaces 41 and 42 together and generates friction between them. The friction inhibits relative rotation between the surfaces 41, 42. The friction is preferably sufficient to prevent rotation and axial movement along the spindle thread in response to axial traction on the spindle 32;

the combined resistance of the threaded spindle 32 and the restraining device 40 is necessary to prevent rotation and axial movement along the spindle thread in response to axial traction on the spindle 32.

The invention claimed is:

1. A self-locking spindle traction mechanism for use in surgical procedures and having an elongated extension that defines a longitudinal axis (L), the spindle traction mechanism comprising:
   an operating end for operating the spindle traction mechanism;
   a connecting end for connecting a surgical accessory;
   a threaded spindle drive, the threaded spindle drive comprising:
      a) a spindle, the spindle having an external thread that extends along the longitudinal axis (L); and
      b) a spindle nut, the spindle nut being seated on the spindle and having an internal thread that engages with the external thread of the spindle;
   a slide, the slide being movable along the longitudinal axis (L) by a relative rotation between the spindle and the spindle nut;
   a drive device, the drive device being situated on said operating end for rotationally driving the threaded spindle drive;
   a gear, the gear being connected between the drive device and the threaded spindle drive, wherein the gear is configured for stepping up the speed of a rotational movement of the drive device and delivering it to the threaded spindle drive, wherein the gear is stepped up in such a way that one revolution of the drive device creates at least two revolutions of the threaded spindle drive,
   a housing, the housing accommodating the threaded spindle drive, and
   a restraining device, the restraining device being configured for inhibiting relative rotation between the spindle and the spindle nut when a tensile force is exerted on the connecting end along the longitudinal axis;
   wherein the restraining device comprises a friction pair;
   wherein the friction pair comprises a first contact surface on a spindle bearing sleeve of the housing, and a second contact surface on a contact disc connected to the spindle, opposite the first contact surface, the contact disc further comprising an opposing surface opposite the second contact surface;
   wherein when a tensile force is exerted on the connecting end along the longitudinal axis, the opposing surface of the contact disc is supported against the gear and the second contact surface is supported against the first contact surface in such a way that frictional resistance is present that prevents an automatic relative rotation between the spindle and the spindle nut due to the tensile force;
   wherein the contact disc rotates with the spindle; and
   wherein the contact disc is rotatable relative to the spindle bearing sleeve.

2. The traction mechanism according to claim 1:
wherein the connecting end is configured for carrying a patient foot holder.

3. The traction mechanism according to claim 1:
wherein the first contact surface and the second contact surface are both substantially perpendicular with respect to the longitudinal axis (L).

4. The traction mechanism according to claim 1:
wherein the spindle is rotatably situated in the housing; and
wherein the spindle nut is rotatably connected to the slide.

5. The traction mechanism according to claim 1,
wherein the spindle bearing sleeve is connected to the housing and surrounds part of the spindle;
wherein the spindle bearing sleeve receives and at least partially surrounds the contact disc when the second contact surface is supported against the first contact surface in such a way that frictional resistance is present that prevents automatic relative rotation between the spindle and the spindle nut due to the tensile force.

6. The traction mechanism according to claim 1:
wherein the connecting end is configured for carrying a patient foot holder;
further comprising a detent mechanism, the detent mechanism being configured to rotate the foot holder about the longitudinal axis (L).

7. The traction mechanism according to claim 1:
wherein a diameter of the spindle is less than 20 mm.

8. The traction mechanism according to claim 1:
wherein the drive device comprises a hand crank.

9. An extension beam for an operating table, comprising:
the traction mechanism according to claim 1;
a bar, the bar being mountable on an operating table;
a strut, the strut connecting the bar and the traction mechanism; and
a holder configured for a foot of a patient, which is connected to the traction mechanism;
   wherein said traction mechanism is configured for adjusting said holder for a foot of a patient relative to said strut in a direction essentially parallel to the longitudinal axis (L) of the traction mechanism.

10. The traction mechanism according to claim 1:
wherein said gear is a planetary gear.

11. A self-locking spindle traction mechanism for use in surgical procedures and having a longitudinal axis (L), the spindle traction mechanism comprising:
   an operating end for operating the spindle traction mechanism;
   a connecting end for connecting a surgical accessory;
   a threaded spindle drive, the threaded spindle drive comprising:
      a) a spindle, the spindle having an external thread that extends along the longitudinal axis (L); and b) a spindle nut, the spindle nut being positioned over the spindle and having an internal thread that engages with the external thread of the spindle;

a slide, the slide being movable along the longitudinal axis (L) by a relative rotation between the spindle and the spindle nut;

a drive device, the drive device being situated on said operating end for rotationally driving the threaded spindle drive;

a gear, the gear being connected between the drive device and the threaded spindle drive;

a housing, the housing accommodating the threaded spindle drive, and a restraining device, the restraining device being configured for inhibiting relative rotation between the spindle and the spindle nut when a tensile force is exerted along the longitudinal axis;

wherein the restraining device comprises a friction pair;

wherein the friction pair comprises a first contact surface, and a second contact surface opposite the first contact surface with the first contact surface and the second contact surface extending essentially perpendicularly with respect to the longitudinal axis;

wherein the second contact surface is on a contact disc having the second contact surface and an opposing surface opposite the second contact surface;

wherein when a tensile force is exerted along the longitudinal axis, the opposing surface of the contact disc is supported against the gear, and the second contact surface of the contact disc is supported against the first contact surface in such a way that frictional resistance is present along a plane that extends essentially perpendicularly with respect to the longitudinal axis that prevents an automatic relative rotation between the spindle and the spindle nut due to the tensile force.

12. The traction mechanism according to claim 11:
wherein the first contact surface is on the housing.

13. The traction mechanism according to claim 11:
wherein the restraining device is configured for inhibiting relative rotation between the spindle and the spindle nut when said tensile force is exerted on the connecting end along the longitudinal axis.

14. The traction mechanism according to claim 11:
wherein the gear is a planetary gear configured for stepping up the speed of a rotational movement of the drive device and delivering it to the threaded spindle drive.

15. The traction mechanism according to claim 11:
wherein the gear is stepped up in such a way that one revolution of the drive device creates at least two revolutions of the threaded spindle drive; and wherein the connecting end is configured for carrying a patient foot holder.

16. The traction mechanism according to claim 11:
wherein the housing comprises a spindle bearing sleeve on which the first contact surface is formed;

wherein the contact disc is connected to and rotates with the spindle;

wherein the contact disc is rotatable relative to the spindle bearing sleeve.

17. An extension beam for an operating table, comprising:
the traction mechanism according to claim 11;
a bar, the bar being mountable on an operating table;
a strut, the strut connecting the bar and the traction mechanism; and
a holder configured for a foot of a patient, which is connected to the traction mechanism;
wherein said traction mechanism is configured for adjusting said holder for a foot of a patient relative to said strut in a direction essentially parallel to the longitudinal axis (L) of the traction mechanism.

18. The traction mechanism according to claim 1, wherein an end of the spindle is supported within the gear at the operating end of the spindle traction mechanism.

19. The traction mechanism according to claim 18, wherein the gear is a planetary gear, the end of the spindle supported within the gear is connected to a sun wheel of the planetary gear, and when the tensile force is exerted along the longitudinal axis, the opposing surface of the contact disc is supported against the sun wheel.

20. The traction mechanism according to claim 11, wherein an end of the spindle is supported within the gear at the operating end of the spindle traction mechanism.

* * * * *